US012582803B2

(12) United States Patent
Scherich et al.

(10) Patent No.: US 12,582,803 B2
(45) Date of Patent: Mar. 24, 2026

(54) CATHETER TIP CONTROL DEVICE AND RELATED SYSTEMS AND METHODS

(71) Applicant: Becton, Dickinson and Company, Franklin Lakes, NJ (US)

(72) Inventors: Megan Scherich, Salt Lake City, UT (US); Weston F. Harding, Lehi, UT (US); Curtis H. Blanchard, Riverton, UT (US); Yiping Ma, Layton, UT (US); John Lackey, West Valley City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 899 days.

(21) Appl. No.: 17/362,630

(22) Filed: Jun. 29, 2021

(65) Prior Publication Data

US 2022/0023592 A1     Jan. 27, 2022

Related U.S. Application Data

(60) Provisional application No. 63/055,216, filed on Jul. 22, 2020.

(51) Int. Cl.
A61M 25/01          (2006.01)
(52) U.S. Cl.
CPC .... A61M 25/0136 (2013.01); A61M 25/0122 (2013.01)
(58) Field of Classification Search
CPC .......... A61M 25/0136; A61M 25/0122; A61M 25/04; A61M 25/02; A61M 25/0097; A61M 25/0074; A61M 25/0082; A61M 25/0102; A61M 2025/0079; A61M 2025/028; A61M 2210/12; A61M 39/20; A61B 5/15074; A61B 5/15003; A61B 5/150221; A61B 5/150992
See application file for complete search history.

(56)          References Cited

U.S. PATENT DOCUMENTS

| | | | | |
|---|---|---|---|---|
| 1,087,845 | A | * | 2/1914 | Stevens .............. A61M 25/0113 604/159 |
| 3,631,848 | A | * | 1/1972 | Muller .............. A61M 25/0905 604/95.04 |
| 4,250,880 | A | | 2/1981 | Gordon |
| 8,920,414 | B2 | | 12/2014 | Stone et al. |
| 2006/0089608 | A1 | * | 4/2006 | Shaykh ................ A61B 17/435 604/264 |

(Continued)

FOREIGN PATENT DOCUMENTS

EP          0023580  A1     2/1981

*Primary Examiner* — James D Ponton
*Assistant Examiner* — John A Doubrava
(74) *Attorney, Agent, or Firm* — The Webb Law Firm

(57)          ABSTRACT

A catheter assembly may include a catheter adapter having a proximal end, a distal end, and a lumen extending therebetween. A wedge adapter may be retained within the lumen and have a wedge coupled thereto. The wedge may be configured to retain an end of a catheter such that a tip of the catheter extends through the distal end of the catheter adapter. A control feature may extend through an end or side wall of the catheter adapter. The control feature may be configured to manipulate the wedge to control a position of the tip of the catheter to open a fluid path within a vasculature.

10 Claims, 7 Drawing Sheets

(56)                    References Cited

U.S. PATENT DOCUMENTS

| 2007/0093778 A1* | 4/2007 | Cindrich | ............... A61M 5/158 |
| | | | 604/500 |
| 2009/0281525 A1 | 11/2009 | Harding et al. | |
| 2011/0071497 A1* | 3/2011 | Alinsod | ............ A61M 25/0014 |
| | | | 604/509 |
| 2013/0102888 A1* | 4/2013 | Slim | ......................... C30B 7/10 |
| | | | 600/424 |
| 2017/0120011 A1 | 5/2017 | Burkholz et al. | |
| 2018/0272106 A1 | 9/2018 | Funk et al. | |
| 2020/0078579 A1 | 3/2020 | Harding et al. | |

* cited by examiner

CATHETER TIP CONTROL DEVICE AND RELATED SYSTEMS AND METHODS

RELATED APPLICATIONS

This application claims benefit of U.S. Provisional Patent Application No. 63/055,216, filed on Jul. 22, 2020, entitled CATHETER TIP CONTROL DEVICE AND RELATED SYSTEMS AND METHODS, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient to obtain a blood sample.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal, fluid infusion, or probe access.

Catheter functionality, however, may be impeded for several reasons, particularly when there is a prolonged dwelling time of the catheter within the vasculature. For example, when the catheter is left inserted in the patient for more than a day, the catheter may become susceptible to complications and obstructions that impede fluid flow. For example, a catheter may become occluded at its tip due to the presence of fibrin sheath or thrombus forming in or on the catheter or on vein walls. As a result, while catheters are commonly used for acquiring a blood sample at a time of catheter placement, they are less commonly used for acquiring a blood sample during the catheter dwell period. When a blood sample is desired during the catheter dwell period, an additional needle stick is typically used to provide vein access for blood collection, causing additional pain for the patient as well as increased material costs. It has been shown, however, that moving or manipulating the catheter or the skin around the catheter, also known as applying traction, to move or re-position the catheter tip within the vein may improve blood draw success and catheter functionality by avoiding occlusions, obstacles and/or thrombus, or by moving the tip to a location which favors improved blood flow.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to catheter assemblies used to infuse fluids and/or collect blood from the vasculature of a patient. Various complications and obstructions may impede fluid flow through the catheter, however, thus compromising catheter functionality and performance. For example, the catheter may become occluded at its tip due to the presence of fibrin sheath, thrombus, vein walls, or valves. Application of traction to the catheter to re-position the catheter tip within the patient's vasculature may significantly improve catheter functionality and blood draw success.

In some embodiments, a catheter assembly to open a fluid path may include a catheter adapter having a proximal end, a distal end, and a lumen extending along a longitudinal axis therebetween. A wedge adapter may be retained within the lumen and have a wedge coupled thereto. In some embodiments, the wedge may be configured to retain an end of a catheter such that a tip of the catheter extends through the distal end of the catheter adapter.

In some embodiments, a control feature may be located at a proximal end of the wedge adapter. The control feature may extend through the proximal end and/or a side wall of the catheter adapter. In some embodiments, the control feature may be configured to manipulate the wedge to control a position of the tip of the catheter to open a fluid path.

In some embodiments, the end of the catheter may be coupled to the wedge via an interference fit. In some embodiments, the wedge may be coupled to the wedge adapter via an interference fit or an adhesive.

In some embodiments, the control feature may include a tab, a handle, a button, and/or a dial. In some embodiments, the tab or the handle may be configured to move in a proximal direction to retract the tip of the catheter relative to the distal end of the catheter adapter. In some embodiments, the tab or the handle may be configured to retract the tip of the catheter relative to a secured portion of the catheter adapter. In some embodiments, the control feature may be moved to reposition the tip of the catheter radially to a more desirable location within a vein. In some embodiments, the control feature may move the tip of the catheter to a previous position or to another position within the vein.

In some embodiments, the tab or the handle may move in a distal direction to advance the tip of the catheter relative to a fixed portion of the catheter adapter or relative to the distal end of the catheter adapter. In some embodiments, the tab or the handle may move in a distal direction to move the tip of the catheter to a previous or another position within the vein.

In some embodiments, the control feature may include the button or the tab and may be configured to be depressed against the wedge to control the position of the tip of the catheter. In some embodiments, the control feature may include the dial and be configured to rotate in a transverse direction relative to the longitudinal axis to control the position of the tip of the catheter.

In some embodiments, the catheter assembly may include a lock element to engage the control feature and/or the wedge adapter to secure the position of the tip of the catheter. In some embodiments, the catheter assembly may further include a septum disposed within the lumen of the catheter adapter to seal the proximal end. In some embodiments, the control feature may be disposed proximal to the septum.

In some embodiments, the catheter adapter may comprise a first section including the distal end and a second section including the proximal end. In some embodiments, the first section may be slidable relative to the second section along the longitudinal axis. In some embodiments, the catheter may extend from the distal end of the first section such that the first section may be moved distally relative to the second section to open the fluid path.

In some embodiments, the catheter assembly may include an outer sleeve extending from the distal end of the catheter adapter. The outer sleeve may be configured to receive the catheter therethrough such that the catheter is slidable within the outer sleeve. In some embodiments, the catheter assembly may include a toggle element having a first portion coupled to the catheter and a second portion coupled to the outer sleeve. In some embodiments, depressing the toggle element may retract the catheter relative to the outer sleeve, and releasing the toggle element may advance the catheter relative to the outer sleeve.

In some embodiments, the catheter assembly to open the fluid path may include the catheter adapter and the catheter extending from the distal end of the catheter adapter. A stationary base element may be configured to receive the catheter adapter such that movement of the catheter adapter relative to the stationary base element controls the position of the tip of the catheter.

In some embodiments, the catheter adapter may be linearly translated along the longitudinal axis to control the position of the tip of the catheter. In some embodiments, the catheter adapter may be configured to rotate in a transverse direction relative to the longitudinal axis to control the position of the tip of the catheter.

In some embodiments, the catheter adapter may include a side port coupled to an extension set, wherein the extension set is configured to rotate in a transverse direction relative to the longitudinal axis to rotate the catheter adapter. In some embodiments, a post may extend through a screw track of the stationary base element and may contact the catheter adapter. In some embodiments, the screw track may extend along a surface of the stationary base element in a direction parallel to the longitudinal axis. The post may be axially translated along the screw track in response to rotation of the catheter adapter.

In some embodiments, the catheter assembly may include a traction projection coupled to a surface of the catheter adapter and/or the stationary base element to facilitate application of traction to the catheter. In some embodiments, the traction projection may include a curved and/or textured distal surface. In some embodiments, the catheter assembly may include a spring or other device or feature to facilitate application of traction to the catheter. In some embodiments, the spring or other device or feature may be pretensioned by other movements.

It is to be understood that both the foregoing general description and the following detailed description are examples and explanatory and are not restrictive of the present disclosure, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

4

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION

As used in this specification, the term "distal" refers to a direction away from a clinician who would place the device into contact with a patient, and nearer to the patient. The term "proximal" refers to a direction nearer to the clinician who would place the device into contact with the patient, and farther away from the patient. Thus, for example, the end of a catheter first touching the body of the patient is the distal end, while the opposite end of the catheter is the proximal end of the catheter.

Figure 1:
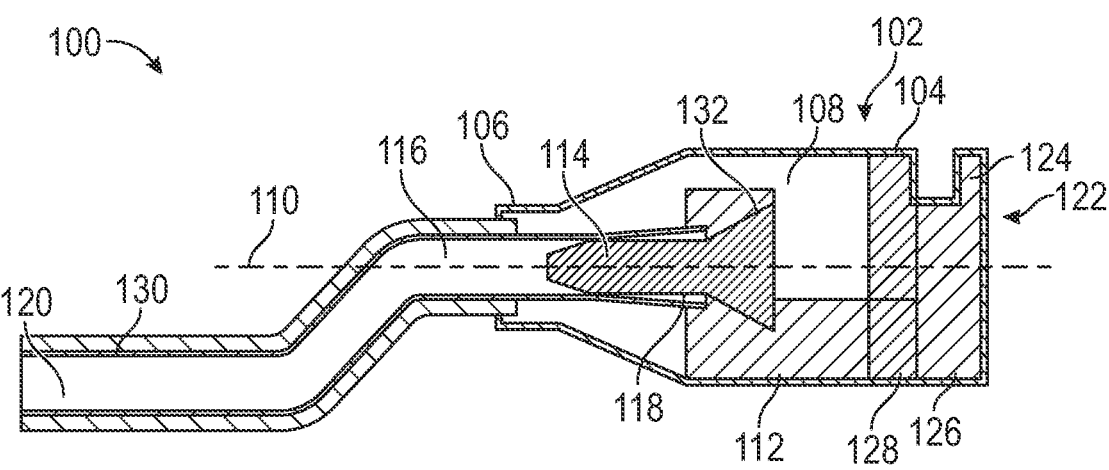
FIG. 1 is a cross-sectional view of an example catheter assembly, illustrating an example wedge adapter and an example control feature comprising a dial according to some embodiments.

Referring now to FIG. 1, in some embodiments, a catheter assembly 100 may be configured to control a location of a tip 120 of a catheter 116 within a patient's vasculature to avoid obstructions and open a fluid path for blood collection or fluid delivery. In some embodiments, the catheter 116 may include a peripheral IV catheter 116, a peripherally-inserted central catheter 116, or a midline catheter 116. In some embodiments, the catheter assembly 100 may have been previously inserted into the vasculature of a patient and may be dwelling within the vasculature. In such cases, the catheter 116 may be susceptible to blockage by debris (e.g., fibrin or thrombus), and/or adhering of the tip 120 of the catheter 116 to the vasculature. Thus, blood withdrawal using the catheter 116 may be difficult.

An example catheter assembly 100 may include a catheter adapter 102 having a proximal end 104, a distal end 106, and a lumen 108 extending along a longitudinal axis 110 therebetween. In some embodiments, as discussed in more detail with reference to FIGS. 8 and 9A, B below, the catheter adapter 102 may further include a side port and integrated extension set for infusion, blood draw, or instrument delivery. In some embodiments, a wedge adapter 112 may be retained within the lumen 108 and may have a wedge 114 coupled thereto. In some embodiments, the wedge adapter 112 may include an opening 132 or recess to receive and retain the wedge 114. In some embodiments, the opening 132 may retain the wedge 114 such that a distal end of the wedge 114 is exposed, thereby facilitating coupling the catheter 116 thereto. In these and other embodiments, the opening 132 may be aligned with the distal end 106 of the catheter adapter 102 such that the tip 120 of the catheter 116 may extend through the distal end 106 upon coupling the catheter 116 to the wedge 114. Some embodiments may couple the wedge 114 to the wedge adapter 112 via an interference fit, an adhesive, and/or any other suitable coupling mechanism.

In some embodiments, a distal end of the wedge 114 may be configured to retain an end 118 of the catheter 116. In some embodiments, for example, the catheter 116 may include an inner diameter that is equal to or greater than a diameter of the wedge 114. In some embodiments, the diameter of the wedge 114 may gradually increase in the proximal direction along the wedge 114 to facilitate coupling the catheter 116 to the wedge 114 via a press or interference fit. In some embodiments, the catheter 116 may be coupled to the wedge via an adhesive or other coupling mechanism. In some embodiments, the end 118 of the catheter 116 may be retained by the distal end of the wedge 114 such that the tip 120 of the catheter 116 extends through the distal end 106 of the catheter adapter 102. In other embodiments, the end 118 of the catheter 116 may be coupled directly to the catheter adapter 102 by an adhesive or other suitable element.

In some embodiments, the catheter assembly 100 may include a control feature 122 to manipulate a position and/or orientation of the wedge 114. In some embodiments, controlling the wedge 114 in this manner may control the tip 120 of the catheter 116. In some embodiments, the control feature 122 may be used to open a fluid pathway by positioning the tip 120 of the catheter 116 to avoid or clear obstructions, thus providing access to the vasculature of the patient without any additional needle sticks. For example, in some embodiments, the control feature 122 may control the position of the tip 120 of the catheter 116 to clear the pathway for collecting a blood sample. In some embodiments, the catheter assembly 100 may be used for needle-free blood collection and/or fluid infusion.

As shown in FIG. 1, in some embodiments, the control feature 122 may include a tab 124 coupled to or integrated with a proximal end of the wedge adapter 112. In some embodiments, the tab 124 may extend beyond the proximal end 104 of the catheter adapter 102 and may be movable along the longitudinal axis 110.

Thus, in operation, a user may grasp and pull the tab 124 in a proximal direction along the longitudinal axis 110 to translate the wedge adapter 112 in a proximal direction along the longitudinal axis 110. In some embodiments, the tab 124 or other control feature 122 may be pulled or extended in a proximal direction beyond the proximal end 104 of the catheter adapter 102. In some embodiments, translation of the wedge adapter 112 may thus translate the wedge 114 in a proximal direction along the longitudinal axis 110 to retract the tip 120 of the catheter 116 within the vasculature. Similarly, in some embodiments, the tab 124 or other control feature 122 may be pushed or moved in a distal direction along the longitudinal axis 110 to thereby translate the wedge adapter 112 and the wedge 114 in a distal direction to advance the tip 120 of the catheter 116 within the vasculature.

In some embodiments, the control feature 122 may include a dial 126 extending from the proximal end of the wedge adapter 112. In some embodiments, the dial 126 may be coupled to or integrated with the tab 124. In operation, in some embodiments, the dial 126 may rotate the wedge adapter 112 and wedge 114 in a transverse direction relative to the longitudinal axis 110. In some embodiments, rotation of the dial 126 in this manner may rotate the tip 120 of the catheter 116 within the vasculature to maneuver the catheter 116 as desired. In some embodiments, the tab 124 and the dial 126 may be used in combination to move the tip 120 of the catheter 116 forward, backward, laterally and/or diagonally within the vasculature. In some embodiments, combined axial and rotational movement of the control feature 122 may maneuver the tip 120 of the catheter 116 in any direction within the vasculature.

As illustrated in these and other embodiments, a septum or fluid seal 128 may be disposed at or within the proximal end 104 of the catheter adapter 102 to close the fluid path. In some embodiments, the control feature 122 and/or the wedge adapter 112 may extend through the fluid seal 128 and permit movement of the control feature 122 relative thereto. In some embodiments, the fluid seal 128 may include silicone, rubber, an elastomer, a plastic and rubber composite, or another suitable material. In some embodiments, the fluid seal 128 may be provided via an interference fit, mechanical threading or other connection, or other suitable feature or mechanism. In some embodiments, the fluid seal 128 may include an aperture, slit, or the like to accommodate the control feature 122 and/or wedge adapter 112 therethrough. In this manner, some embodiments of the control feature 122 may manipulate the position of the tip 120 of the catheter 116 while maintaining a closed fluid path.

In some embodiments, as discussed in more detail below, the catheter assembly 100 may include an outer sleeve 130 coupled to the distal end 106 of the catheter 116 such that the catheter 116 may be received within the outer sleeve 130 and may extend longitudinally therethrough. In some embodiments, the catheter 116 may be independently movable within the outer sleeve 130. In some embodiments, a lubricant or other suitable coating may be applied between the catheter 116 and the outer sleeve 130 to reduce friction between the two. In other embodiments, the catheter assembly 100 may include an independent catheter 116 without an outer sleeve 130. In some embodiments, the catheter 116 and/or the outer sleeve 130 may include an antithrombogenic material to reduce the formation of thrombus.

Figure 2A:
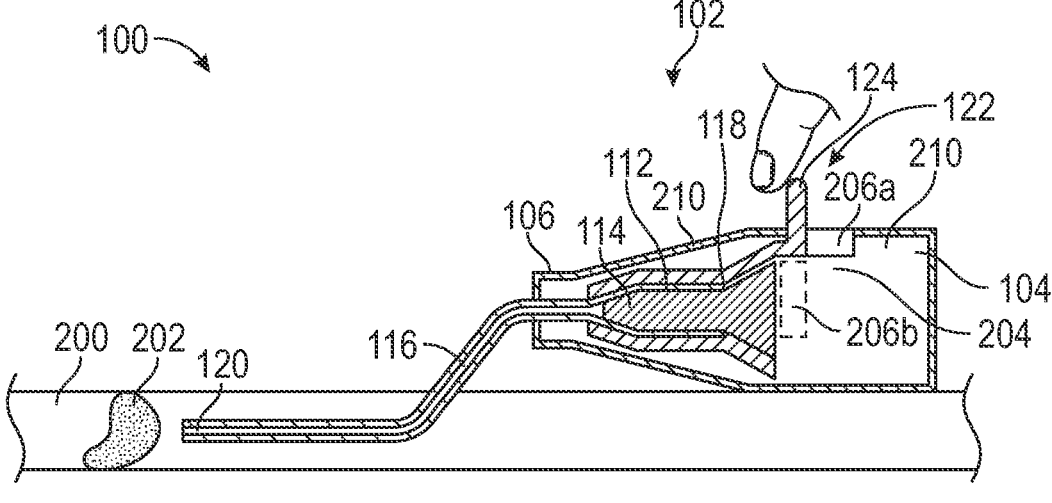
FIG. 2A is a cross-sectional view of another example catheter assembly, illustrating another example control feature comprising a tab actuator according to some embodiments.
Figure 2B:
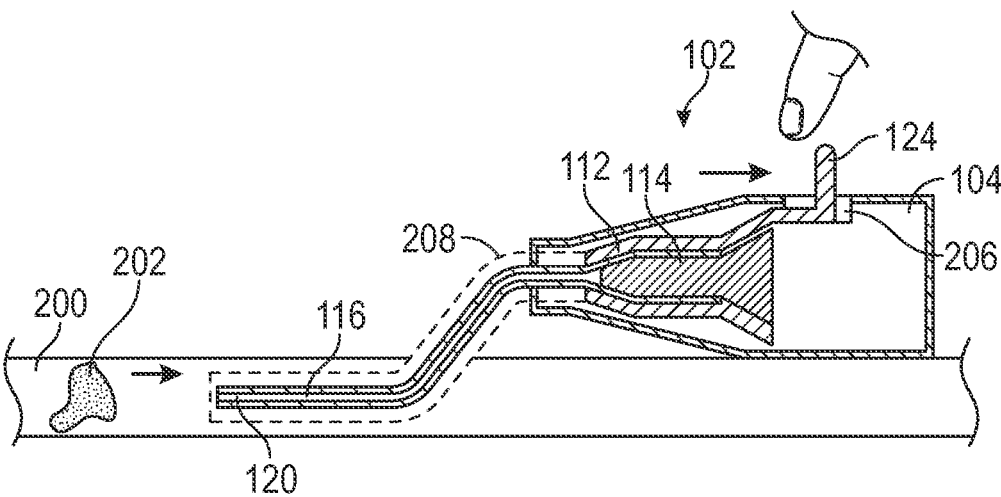
FIG. 2B is a cross-sectional view of the catheter assembly of FIG. 1A, illustrating retraction of the tab actuator according to some embodiments.

Referring now to FIGS. 2A and 2B, some embodiments of a control feature 122 may include the tab 124 coupled to the wedge adapter 112 such that the tab 124 extends through a side wall 204 of the catheter adapter 102. In some embodiments, at least a portion of the wedge adapter 112 may circumscribe or grip at least a portion of the end 118 of the catheter 116 retained by the wedge 114. In this manner, some embodiments of the wedge adapter 112 may further secure the end 118 of the catheter 116 onto the wedge 114. In operation, in some embodiments, a user may manipulate the position and/or orientation of the tab 124 to manipulate the position of the wedge 114 in the same manner.

As shown in FIG. 2A, for example, the tab 124 may project through a slot 206 extending longitudinally along an outer surface of the side wall 204. In some embodiments, the tab 124 may be movable along a length of the slot 206 such that translating the tab 124 in a distal direction may also translate the wedge adapter 112 and wedge 114 in a distal direction within the lumen 108, thereby advancing the tip 120 of the catheter 116 within the vasculature. Likewise, translating the tab 124 in a proximal direction along the slot 206 may translate the wedge adapter 112 and wedge 114 proximally to retract the tip 120 of the catheter 116 within the vasculature. In some embodiments, the slot 206 may be disposed around a circumference of the side wall 204 such that the tab 124 may be rotated to produce rotational movement of the tip 120 of the catheter 116 within the vasculature.

In some embodiments, the slot 206 may extend along an outer surface 210 of the catheter adapter 102 side wall 204 in a direction transverse to the longitudinal axis 110. In some embodiments, the slot 206 may comprise an "L" shape such that one portion of the slot 206a extends along the outer surface 210 in a direction parallel to the longitudinal axis 110, and a second portion of the slot 206b extends in a direction transverse to the longitudinal axis 110. In any case, in some embodiments, translation of the tab 124 along the slot 206 in a direction transverse to the longitudinal axis 110 may rotate the associated wedge adapter 112 and wedge 114 to rotate the catheter 116 tip 120 within the vasculature.

Some embodiments of the catheter assembly 100 may include an outer sleeve 208 extending from the distal end 106 of the catheter adapter 102. In some embodiments, as shown in FIG. 2B, the outer sleeve 208 may be coupled to a distal end 118 of the catheter adapter 102 such that at least a portion of the catheter 116 may extend therethrough. In some embodiments, the outer sleeve 208 may be coupled to the catheter adapter 102 via an interference fit, a bushing, an adhesive, or other suitable technique or device. In some embodiments, the outer sleeve 208 may thus remain in place when the catheter 116 is moved, reducing a risk of phlebitis, dislodgment, and/or microbial ingress.

Figure 3:
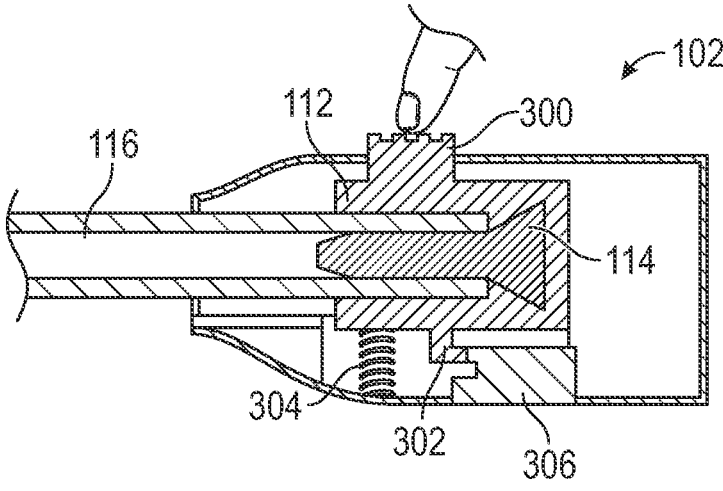
FIG. 3 is a cross-sectional view of an example control feature comprising a push button actuator according to some embodiments.

Referring now to FIG. 3, in some embodiments, the control feature 122 may include a push button 300 extending from the wedge adapter 112 through the top surface 408 of the catheter adapter 102. In this manner, the push button 300 may be accessible via an exterior of the catheter adapter 102 and may be actuated by depressing the button 300 in a downward direction perpendicular to the longitudinal axis 110. In some embodiments, the push button 300 may extend laterally through the side wall 204 or proximal end 104 of the catheter adapter 102. In these and other embodiments, the push button 300 may be actuated by depressing a top surface of the push button 300 in a lateral direction against an outer surface of the side wall 204, or by depressing a side surface of the push button 300 in a downward direction perpendicular to the longitudinal axis 110 like a lever.

In these and other embodiments, the push button 300 may be configured to be pressed against the wedge 114 to control the position of the tip 120 of the catheter 116. In some embodiments, the push button 300 may urge the wedge 114 and end 118 of the catheter 116 in a downward direction, thereby causing the tip 120 of the catheter 116 to move in an upward direction within the vasculature.

In some embodiments, the wedge adapter 112 may include a biasing element 304 or spring disposed between the wedge adapter 112 and the catheter adapter 102 such that depressing the push button 300 compresses the biasing element 304. Similarly, releasing the push button 300 may release compression of the biasing element 304 such that the biasing element 304 urges the wedge adapter 112 in an upward direction to its initial starting position.

In some embodiments, the wedge adapter 112 may include a lock element 302 to selectively secure a position of the wedge adapter 112 with respect to the catheter adapter 102. In some embodiments, as shown in FIG. 3, the lock element 302 may include a protrusion extending from a lower edge of the wedge adapter 112. In some embodiments, the lumen 112 of the catheter adapter 102 may include a corresponding lock feature 306 such as a groove or other suitable feature. The lock feature 306 of the catheter adapter 102 may selectively engage the lock element 302 of the wedge adapter 112 via a snap fit, for example, to prevent movement of the tip 120 of the catheter 116 within the vasculature.

In operation, some embodiments of the push button 300 may be depressed to urge the wedge adapter 112 downward against the biasing element 304. Further, in some embodiments, the push button 300 may be tilted downward or translated in a proximal direction such that the lock element 302 engages the corresponding lock feature 306. In this manner, the lock element 302 may secure the position of the tip 120 of the catheter 116 within the vasculature. In some embodiments, the lock element 302 may be released from the lock feature 306 in a similar manner. Specifically, in some embodiments, the push button 300 may be depressed such that the wedge adapter 112 is depressed against the biasing element 304. In some embodiments, the push button 300 may be tilted or urged in a distal direction to disengage the lock element 302 from the lock feature 306. The biasing element 304 may then urge the wedge adapter 112 upward to its initial position.

Figure 4A:
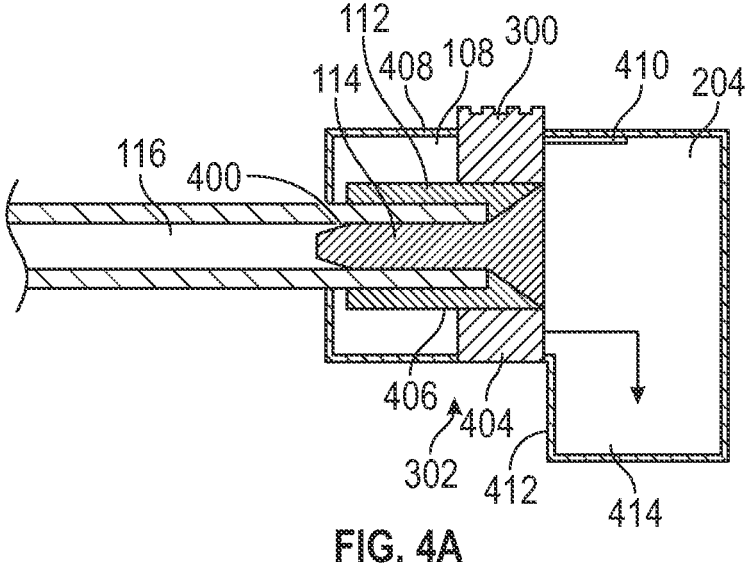
FIG. 4A is a cross-sectional view of another example control feature comprising a slide actuator and wedge adapter according to some embodiments.
Figure 4B:
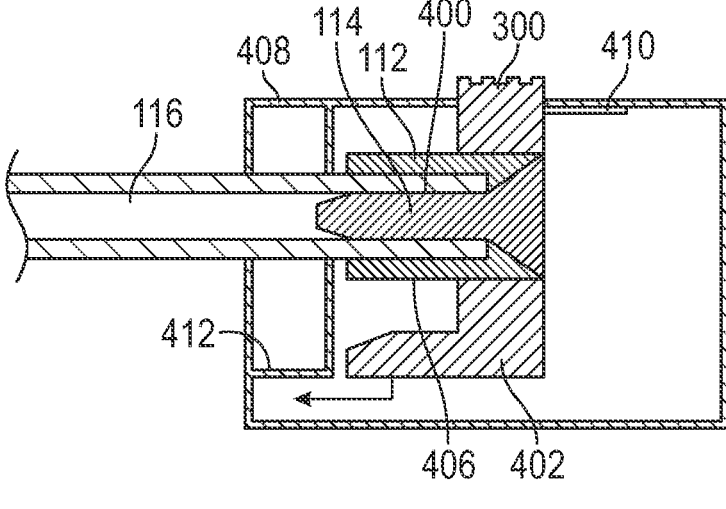
FIG. 4B is a cross-sectional view of another example control feature including a lock element according to some embodiments.

FIGS. 4A and 4B illustrate alternative embodiments of the catheter assembly 100 including the push button 300 extending from the wedge adapter 112. As shown in FIG. 4A, in some embodiments, the control feature 122 may include the push button 300 extending from the wedge adapter 112 and through a top surface 408 of the catheter adapter 102 such that it is accessible via the exterior of the catheter adapter 102. In some embodiments, the push button 300 may extend through the side wall 204 or the proximal end 104 of the catheter adapter 102. In some embodiments, the push button 300 may extend through a slot 410 in the catheter adapter 102 such that the push button 300 may be translated along the slot 410 to translate the wedge adapter 112 within the lumen 108.

As shown in FIG. 4A, the wedge adapter 112 may be disposed in the lumen 108 of the catheter adapter 102 and may include a recess 400 having a size and shape configured to receive and retain the wedge 114. In some embodiments, the recess 400 may retain the wedge 114 via an interference fit, an adhesive, or any other suitable fastener device or mechanism.

In some embodiments, the recess 400 may substantially align with the distal end 106 of the catheter adapter 102 such that the distal end of the wedge 114 may retain the end 118 of the catheter 116 and the tip 120 of the catheter 116 may extend through the distal end 106 of the catheter adapter 102. As shown, in some embodiments, the wedge adapter 112 may extend substantially perpendicularly relative to the longitudinal axis 110.

In some embodiments, the wedge adapter 112 may include a lock element 302 to secure a position of the wedge adapter 112 and wedge 114 within the lumen 108. For example, as shown in FIG. 4A, the lock element 302 may include a proximal portion 404 extending perpendicularly from a lower edge 406 of the wedge adapter 112. In some embodiments, upon actuating the push button 300, the push button 300 may be translated along a channel 410 in a proximal direction, thereby translating the wedge adapter 112 in a proximal direction within the lumen 108. In some embodiments, the proximal portion 404 of the wedge adapter 112 may engage a recess 414 formed by a shoulder 412 of the lumen 108, thereby causing the wedge 114 to misalign with the distal end 106 of the catheter adapter 102 to secure a position of the tip 120 of the catheter 116 within the vasculature.

In some embodiments, as shown in FIG. 4B, the lock element 302 may include a leg 402 extending distally from the proximal portion 404 in a direction parallel to the longitudinal axis 110. In some embodiments, depressing the push button 300 in a downward direction may also urge the wedge adapter 112 downward, causing the wedge adapter 112 and wedge 114 to misalign with the distal end 106 of the catheter adapter 102. In some embodiments, depressing the push button 300 in this manner may cause the leg 402 to align with a channel 410 in the lumen 108.

In some embodiments, the push button 300 may then be translated in a distal direction along the slot 206 to thereby translate the leg 402 of the wedge adapter 112 in a distal direction to engage the channel 410 within the lumen 108. In some embodiments, this may secure a position of the tip 120 of the catheter 116 within the vasculature.

Figures 5, 6A:
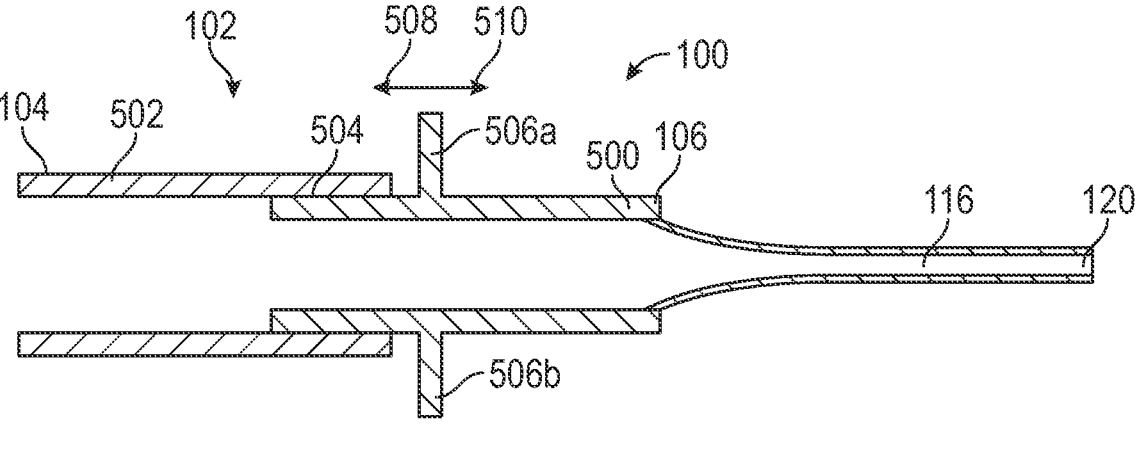
FIG. 5 is a cross-sectional view of an example catheter adapter having slidable sections according to some embodiments.
FIG. 6A is a cross-sectional view of an example toggle element coupled to an outer sleeve and to a catheter according to some embodiments.

Referring now to FIG. 5, in some embodiments, the catheter adapter 102 may comprise a first section 500 including the distal end 106 and a second section 502 including the proximal end 104. In some embodiments, the catheter 116 may extend from the distal end 106 of the first section 500. In some embodiments, the first section 500 may be axially slidable relative to the second section 502. In this manner, in some embodiments, the first section 500 may be moved in a proximal direction 508 relative to the second section 502 to retract the tip 120 of the catheter 116 within the vasculature, or may be moved in a distal direction 510 relative to the second section 502 to advance the tip 120 of the catheter 116 within the vasculature.

In some embodiments, a flexible joint 504 may be incorporated between the first section 500 and the second section 502. The flexible joint 504 may comprise a flexible polymer or other suitable material to provide flexibility and controlled relative motion between the first section 500 and the second section 502, thereby facilitating the application of traction to the catheter 116. In some embodiments, for example, the flexible joint 504 may include a short piece of rubber or other suitable material or device.

In some embodiments, the catheter assembly 100 may include one or more grip elements 506a, b coupled to or integrated with the first section 500 and/or the second section 502 to facilitate moving the first section 500 and the second section 502 relative to each other to apply traction to the catheter 116. In some embodiments, the grip element 506a, b may include a projection, an indentation, a tab, a handle, a raised and/or textured surface, or other suitable feature or element to promote a reliable grip.

Figure 6B:
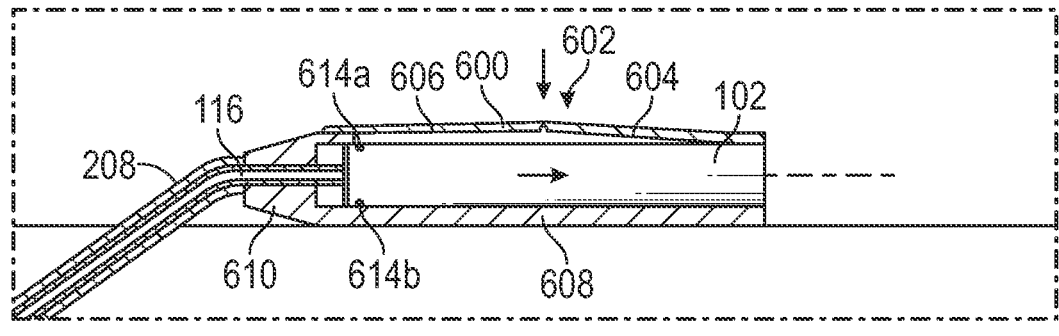
FIG. 6B is a cross-sectional view of the toggle element of FIG. 6A, illustrating the toggle element in an extended position according to some embodiments.

Referring now to FIGS. 6A and 6B, in some embodiments, a stationary base element 608 may secure a position of the catheter adapter 102 relative to the patient. In some embodiments, the stationary base element 608 may be configured to permit the catheter adapter 102 to move relative to the stationary base element 608 such that movement of the catheter adapter 102 may control the position of the tip 120 of the catheter 116 within the vasculature.

In some embodiments, an outer sleeve 208 may extend from the distal end 106 of the catheter adapter 102 or, in some embodiments, from the distal end 610 of the stationary base element 608. Some embodiments of the outer sleeve 208 include at least a portion which may remain stationary within the vasculature. In some embodiments, an end 612 of the outer sleeve 208 may be coupled to the catheter adapter 102 or stationary base element 608 via an adhesive, a bushing, an interference fit, or by any other suitable method or device.

In some embodiments, the outer sleeve 208 may include an inner diameter sufficient to accommodate an outer diameter of the catheter 116 such that the outer sleeve 208 may receive the catheter 116 therethrough. In some embodiments, the outer sleeve 208 may include a length approximating a length of the catheter 116. In some embodiments, the length of the outer sleeve 208 may be less than the length of the catheter 116 such that the tip 120 of the catheter 116 may extend distally beyond the outer sleeve 208.

In some embodiments, the catheter 116 may be axially slidable within the outer sleeve 208. In some embodiments, the catheter assembly 100 may include a toggle element 602 to facilitate translating the catheter 116 relative to the outer sleeve 208, thereby applying traction to the catheter 116 within the vasculature. The toggle element 602 may also reduce a risk of contamination from manipulating the catheter 116 within the vasculature. As shown in FIG. 6A, the catheter adapter 102 may be disposed on top of the stationary base element 608 and the outer sleeve 208 may be coupled to a distal end 610 of the stationary base element 608 such that the outer sleeve 208 aligns with the catheter 116 of the catheter adapter 102. In this manner, in some embodiments, the catheter 116 of the catheter adapter 102 may be received by the outer sleeve 208 of the stationary base element 608. In some embodiments, one or more seal elements 614a, b may be disposed between the stationary base element 608 and the catheter adapter 102 to seal a fluid path between the catheter 116 and the outer sleeve 208.

In some embodiments, the toggle element 602 may include a resilient or flexible arm 600 having a first portion 604 coupled to the catheter adapter 102 and a second portion 606 coupled to the stationary base element 608. In some embodiments, the toggle element 602 may axially translate the catheter adapter 102 in a proximal and/or distal direction relative to the stationary base element 608. In some embodiments, the toggle element 602 may rotate the catheter adapter 102 transversely relative to the stationary base element 608.

As shown in FIGS. 6A and 6B, in some embodiments, depressing the flexible arm 600 may urge the first portion 604 and associated catheter adapter 102 in a proximal direction relative to the stationary base element 608, thereby retracting the catheter 116 relative to the outer sleeve 600. Similarly, in some embodiments, releasing downward pressure on the flexible arm 600 may move the first portion 604 of the flexible arm 600 and associated catheter adapter 102 in a distal direction relative to the stationary base element 608, thereby advancing the catheter 116 relative to the outer sleeve 600. Alternatively, in some embodiments, the first portion 604 and/or the second portion 606 of the flexible arm 600 may be manually or automatically manipulated to move the catheter adapter 102 to retract, advance or rotate the tip 120 of the catheter 116 within the vasculature. In any case, in some embodiments, the outer sleeve 208 may remain fixed within the vasculature such that the insertion site may be unaffected by the movement of the catheter 116.

Figure 7:
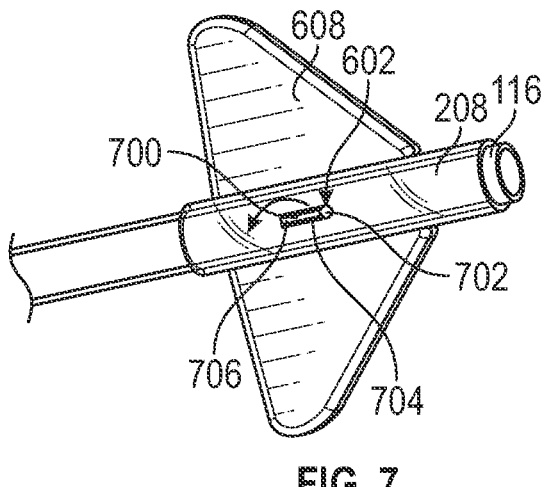
FIG. 7 is an upper perspective view of another example toggle element according to some embodiments.

Referring now to FIG. 7, in some embodiments, the toggle element 602 may include a switch element 700 coupled to the catheter 116 and extending through an aperture 702 in the outer sleeve 208. In some embodiments, a lower end 704 of the switch element 700 may be coupled to the catheter 116 such that an upper end 706 of the switch element 700 may toggle between a first position and a second position to translate the catheter 116 relative to the outer sleeve 208.

In some embodiments, a user may toggle the switch element 700 between the first position and the second position to verify the presence of blood flashback within the catheter adapter 102 in each position. In this manner, the switch element 700 may be used to confirm that applying traction to the catheter 116 by retracting and/or advancing the catheter 116 within the vasculature will not compromise placement of the catheter 116 in the vein.

Figure 8:
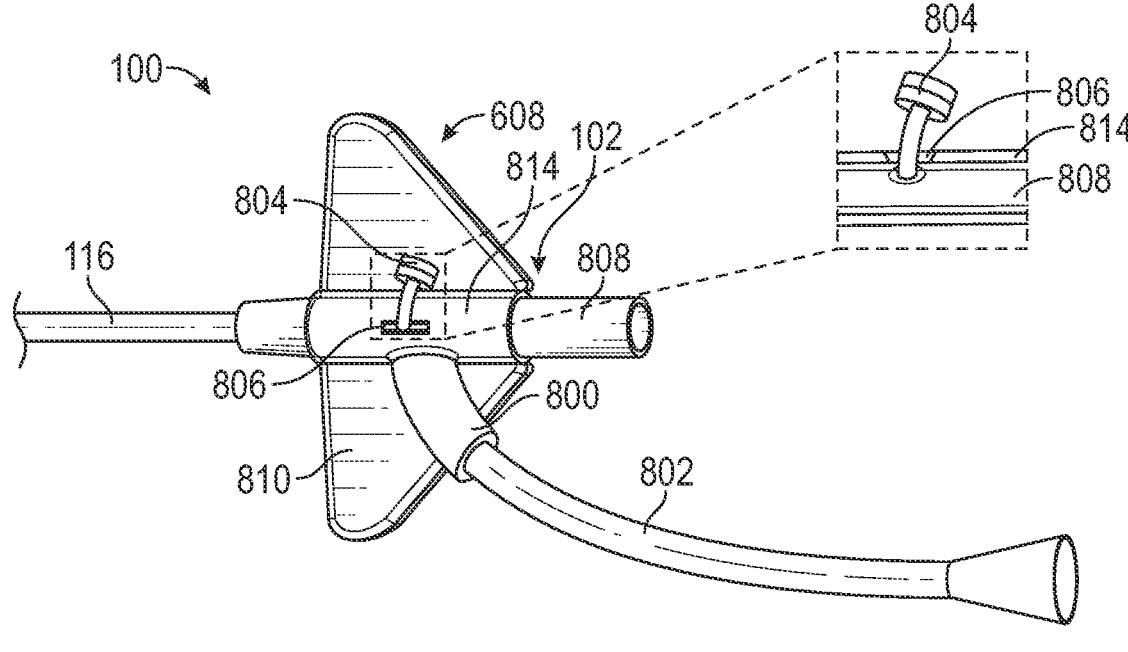
FIG. 8 is an upper perspective view of another example catheter assembly including an example stationary base element and an example catheter adapter having an extension set according to some embodiments.

Referring now to FIG. 8, in some embodiments, the catheter adapter 102 may include a side port 800 coupled to an extension set 802. In some embodiments, the stationary base element 608 may be stationary or fixed relative to the patient via an adhesive applied to its bottom surface, for example. In some embodiments, the stationary base element 608 may be configured to retain the catheter adapter 102 such that it may rotate relative to the stationary base element 608 and longitudinal axis 110. In some embodiments, the catheter adapter 102 may be translated in a distal or proximal direction relative to the stationary base element 608 to apply traction to the catheter 116 within the vasculature.

In some embodiments, the catheter adapter 102 may include a fixed outer portion 814 retaining a rotatable inner portion 808. The rotatable inner portion 808 may include the wedge adapter 112, the wedge 114, and/or the end 118 of the catheter 116. In some embodiments, the inner portion 808 may include a pin, screw, post 804, or other suitable element coupled to an exterior surface thereof and extending in a perpendicular direction relative to the longitudinal axis 110. In some embodiments, the post 804 or other suitable element may extend through a track or groove 806 of the fixed outer portion 814.

In some embodiments, the inner portion 808 may rotate within the outer portion 814 such that the post 804 turns within the groove 806 of the outer portion 814. In some embodiments, rotation of the catheter adapter 102 may rotate or twist the inner portion 808 relative to the outer portion 814, thereby retracting the catheter 116 within the vasculature. In some embodiments, reversing the direction of rotation of the catheter adapter 102 may advance the inner portion 808 relative to the outer portion 814, thereby advancing the catheter 116 within the vasculature.

In some embodiments, the groove 806 may extend longitudinally along an exterior surface of the outer portion 814 of the catheter adapter 102. In operation, in some embodiments, rotation of the inner portion 808 of the catheter adapter 102 relative to the outer portion 814 of the catheter adapter 102 may cause the post 804 to be axially translated along the groove 806 in a proximal direction.

Figure 9A:
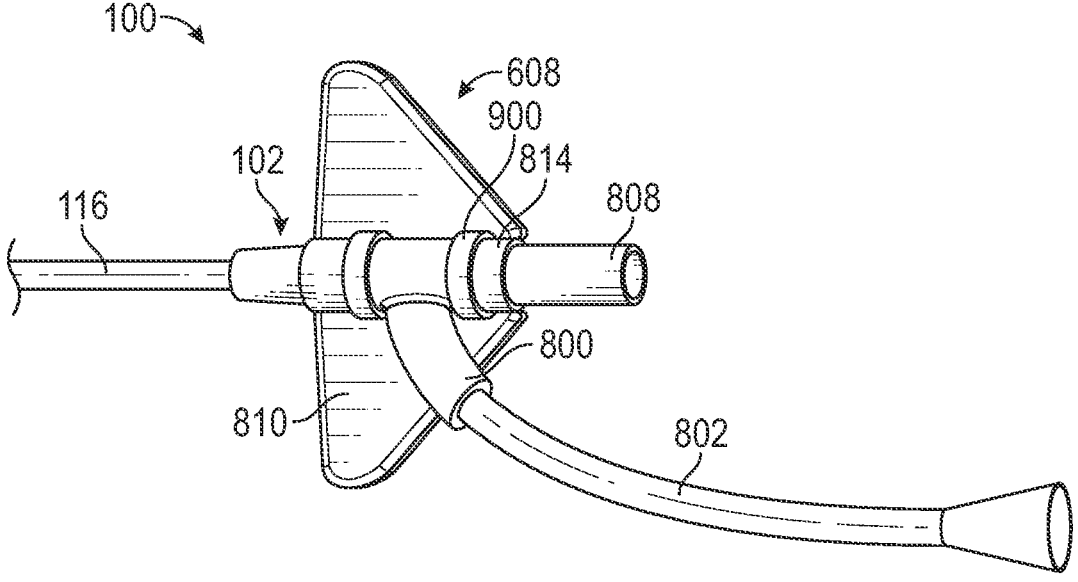
FIG. 9A is an upper perspective view of another example catheter assembly including another example stationary base element and example catheter adapter according to some embodiments.
Figure 9B:
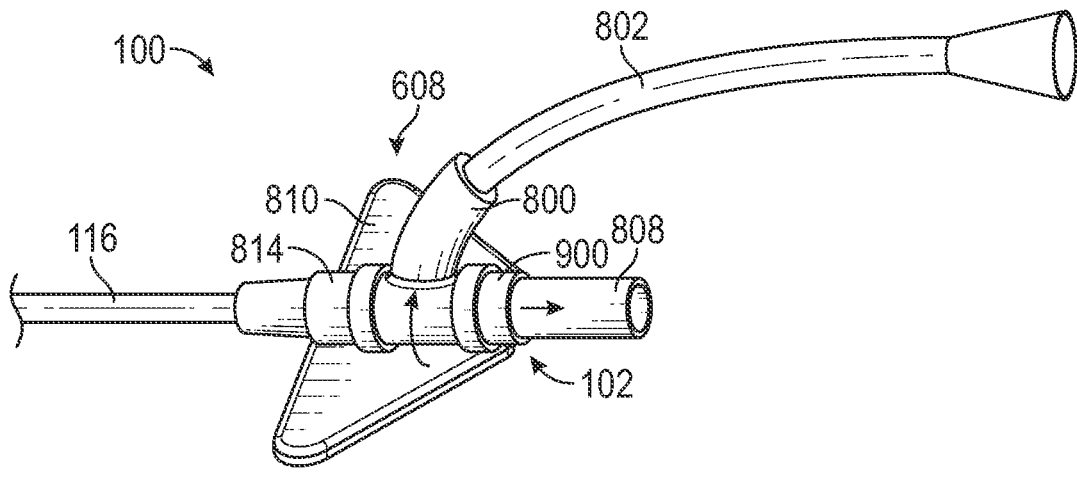
FIG. 9B is an enlarged perspective view of the catheter assembly of FIG. 9A, illustrating rotation of the catheter adapter relative to the stationary base element according to some embodiments.

Referring now to FIGS. 9A and 9B, in some embodiments, the stationary base element 608 may include one or more retaining bands 900, a retaining channel, or other suitable retaining element to rotatably retain the catheter adapter 102 relative to the stationary base element 608. In some embodiments, the retaining bands 900 may be centrally located relative to the stationary base element 608 and may extend in a substantially transverse direction over the catheter adapter 102. In other words, the retaining bands 900 may extend perpendicularly or diagonally over the catheter adapter 102 with respect to its longitudinal axis 110, thereby permitting the catheter adapter 102 to rotate relative to the stationary base element 608. In some embodiments, the wings 810 of the stationary base element 608 may be disposed on opposite sides of the catheter adapter 102 to stabilize the catheter adapter 102 as it moves.

In some embodiments, one or more retaining bands 900 may be disposed adjacent to the side port 800 of the catheter adapter 102. In some embodiments, the side port 800 may be disposed between one or more the retaining bands 900 to stabilize rotation of the side port 800 within the retaining bands 900. In some embodiments, rotating the side port 800 relative to the stationary base element 608 may cause the catheter adapter 102 to rotate in the same manner. In some embodiments, the extension set 802 may be coupled to the side port 800 to facilitate such rotation. For example, in some embodiments, a user may grasp the extension set 802 to rotate the side port 800 and associated catheter adapter 102.

In any case, rotating the catheter adapter 102 in one direction may translate the catheter adapter 102 in a proximal direction relative to the stationary base element 608, thereby retracting the catheter 116 within the vasculature. Similarly, rotating the catheter 116 in an opposite direction may translate the catheter adapter 102 in a distal direction relative to the stationary base element 608, thereby advancing the catheter 116 within the vasculature.

Figure 10:
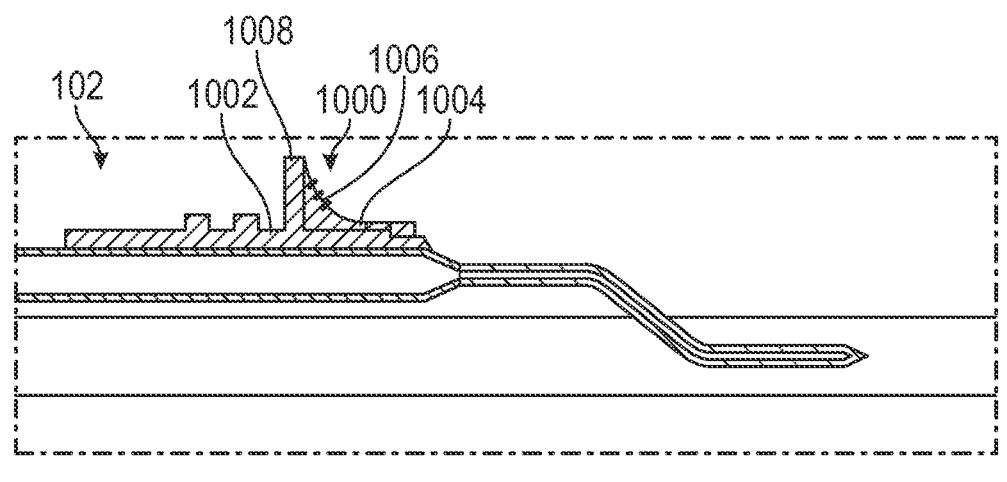
FIG. 10 is a perspective view of an example catheter assembly having an example traction projection according to some embodiments.

Referring now to FIG. 10, in some embodiments, the catheter assembly 100 may include a traction grip 1000 as a standalone feature, or a feature that may be coupled to or integrated with an exterior surface 1002 of the catheter adapter 102 and/or the stationary base element 700 to facilitate application of traction to the catheter 116. In some embodiments, the traction grip 1000 may be curved or may include another suitable shape to facilitate a reliable grasp. In some embodiments, the traction grip 1000 may include one or more roughened or textured surfaces to increase friction to thereby facilitate a reliable grasp. In some embodiments, the textured surface may include ridges, bumps, indentations, or other suitable textural features. In some embodiments, the traction grip 1000 may include one or more markings 1006 to indicate finger placement, thereby facilitating consistency in traction application.

As shown in FIG. 10, in some embodiments, the traction grip 1000 may include a tall tab 1008 or projection integrated with the exterior surface 1002 of the catheter adapter 102 at its distal end 106. In some embodiments, the tall tab 1008 may include a distal surface 1004 that is curved in a proximal direction to facilitate traction application to the catheter 116. In some embodiments, the distal surface 1004 may be roughened or otherwise textured and may be marked with one or more indicator markings 1006 for consistency in traction application location.

All examples and conditional language recited herein are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A catheter assembly to open a fluid path, comprising:
a catheter adapter configured to be (i) secured exterior to a patient and (ii) remain external to the patient, the catheter adapter comprising a proximal end, a distal end, and a lumen extending along a longitudinal axis therebetween;
a wedge adapter retained within the lumen of the catheter adapter and having a wedge coupled thereto, wherein the wedge is configured to be retained within the catheter adapter and external to the patient, wherein the wedge is configured to retain a proximal end of a catheter within the catheter adapter and external to the patient such that a portion of the catheter extends from the distal end of the catheter adapter, wherein the portion of the catheter that extends from the distal end of the catheter adapter is configured to remain in the patient while the catheter adapter is secured exterior to the patient, wherein a portion of the wedge is positioned within the proximal end of the catheter; and
a control feature extending from the wedge adapter and through one of the proximal end and a side wall of the catheter adapter, wherein the control feature is configured to manipulate the wedge to control a position of a tip of the catheter to open a fluid path.

2. The catheter assembly of claim 1, wherein the proximal end of the catheter is coupled to the wedge via an interference fit.

3. The catheter assembly of claim 1, wherein the wedge is coupled to the wedge adapter via one of an interference fit and an adhesive.

4. The catheter assembly of claim 1, wherein the control feature comprises at least one of a tab, a handle, a button, and a dial.

5. The catheter assembly of claim 4, wherein at least one of the tab and the handle is configured to move in a proximal direction to retract the tip of the catheter relative to the distal end of the catheter adapter, and configured to move in a distal direction to advance the tip of the catheter relative to the distal end of the catheter adapter.

6. The catheter assembly of claim 4, wherein at least one of the button and the tab is configured to be depressed against the wedge to control the position of the tip of the catheter.

7. The catheter assembly of claim 4, wherein the dial is configured to rotate in a transverse direction relative to the longitudinal axis to control the position of the tip of the catheter.

8. The catheter assembly of claim 1, further comprising a lock element to engage at least one of the control feature and the wedge adapter to secure the position of the wedge adapter with respect to the catheter adapter.

9. The catheter assembly of claim 1, further comprising a septum disposed within the lumen of the catheter adapter to seal the proximal end of the catheter adapter, wherein the control feature is disposed proximal to the septum.

10. The catheter assembly of claim 1, further comprising an outer sleeve extending from the distal end of the catheter adapter and configured to receive the catheter therethrough, wherein the catheter is slidable within the outer sleeve.

* * * * *